US006511672B2

(12) United States Patent
Tan et al.

(10) Patent No.: US 6,511,672 B2
(45) Date of Patent: Jan. 28, 2003

(54) COMPOSITIONS CONTAINING OPTICAL DIFFUSING PIGMENTS

(75) Inventors: Manuel L. Tan, Westbury, NY (US); Isaac David Cohen, Brooklyn, NY (US); Marie Albers, West Islip, NY (US); Jennifer Oko, Stony Brook, NY (US)

(73) Assignee: Color Access, Inc., Melville, NY (US)

( * ) Notice: Subject to any disclaimer, the term of this patent is extended or adjusted under 35 U.S.C. 154(b) by 9 days.

(21) Appl. No.: 09/764,027

(22) Filed: Jan. 17, 2001

(65) Prior Publication Data

US 2002/0141957 A1 Oct. 3, 2002

(51) Int. Cl.$^{7}$ ............................ A61K 6/00; A61K 7/00; A61K 7/021; A61K 7/035

(52) U.S. Cl. ............................ 424/401; 424/63; 424/69

(58) Field of Search ............................ 424/401, 63, 69, 424/78.03

(56) References Cited

U.S. PATENT DOCUMENTS 4,116,628 A * 9/1978 Hesse et al. ................ 427/154
6,117,435 A * 9/2000 Painter et al. .............. 424/401

OTHER PUBLICATIONS

Emmert, Dr. R., "Quantification of the Soft–Focus Effect" Cosmetics & Toiletries, vol. 111, No. 7, p. 57 (Jul. 1996).

* cited by examiner

*Primary Examiner*—Thurman K. Page
*Assistant Examiner*—S. Howard
(74) *Attorney, Agent, or Firm*—Dorene M. Price, Esq.; Karen A. Lowney, Esq.

(57) ABSTRACT

The present invention provides a method of preventing the appearance of fine lines, wrinkles and discoloration on the skin. This is achieved by the topical application to the skin of a composition containing a first platelet of alumina treated with a metal oxide, a second platelet treated with a spherical scattering component, and a cosmetic or pharmaceutical carrier. The compositions can also contain a standard interference pigment, such as a white and a yellow interference pigment to further blend the color to closely match the natural skin tone. The combination of pigments and platelets creates a mosaic of color and optically manipulates light such that lines, wrinkles, disfigurations and discolorations on the skin appear to substantially vanish. In addition to the pigments and platelet components, a non-interference pigment can also be added to fine-tune the matching of color to the skin tone. The alumina platelet alone is metallic-looking; however, when it is tempered with the other platelet containing the spherical scattering component, the net effect is that the skin appears natural, luminous and flawless.

21 Claims, No Drawings

COMPOSITIONS CONTAINING OPTICAL DIFFUSING PIGMENTS

FIELD OF THE INVENTION

The present invention relates to compositions containing various pigments which manipulate light. More specifically, the invention relates to compositions containing pigments which optimize the optical diffusion effect of light, and consequently cause the appearance of wrinkles, lines and discolorations to vanish and make the skin surface appear luminous, natural and flawless.

BACKGROUND OF THE INVENTION

Makeup and foundation are used to create the appearance of an even skin tone. However, many users complain that these cosmetic products accentuate the appearance of their wrinkles and fine lines. This occurs because makeup builds up inside the crevice formed by the wrinkle. Traditional makeup products contain iron oxides as pigments to match the color of the skin. Iron oxides, inherently particulate, migrate into the crevice formed by a wrinkle or fine line in the skin. Therefore, when the makeup is initially applied, and after application, the makeup spreads on the skin, fills in the line, and in effect, highlights the wrinkle. As a result, the undesirable wrinkles, or flaws, are more noticeable. Because of this phenomenon, many users refrain from using makeup altogether, or do not apply makeup around, for example, their eye area because this region of the skin tends to have more fine lines and wrinkles, such as crows feet. Thus, using traditional pigments alone, the desired result of makeup, to provide an smooth and even looking skin tone, is defeated.

Even when makeup is not used on the skin, lines and wrinkles are visible on the skin and are considered, in a society that aims to achieve eternal youth, or at least the appearance of such, unattractive. The prominent appearance of lines and wrinkles on the skin is due to optical geometry. When light is directed in the direction of an object several events can occur depending on the nature of the object. One is the light can be directed as a reflection completely in one direction determined by the angle of incidence. This is similar to the well-known reflection phenomenon seen with a mirror. Another occurrence is the light can scatter in many different directions, or in a manner referred to as diffuse reflection. And also, the light can transmit through the object, if the object possesses sufficient transparency. This phenomenon also involves the refraction of light. As the light passes through the object its speed (or velocity) and wavelength changes according to the index of refraction, defined by the ratio of the speed of light in vacuum to the speed of light in the object. The light bends as it passes through the object.

When the surface of the skin is smooth, light is absorbed, reflected and scattered off the skin and is observed as a color according to how much light is absorbed and scattered. However, when light is directed toward a wrinkle it is unable to be reflected or even scattered in a way that is observable to the eye except as darkness or the absence of light. The light is non-reflected (in effect it is absorbed) because it becomes trapped inside of the crevice of the wrinkle, similar to the inorganic pigments. Therefore, light bounces inside the crevice but cannot reflect back out to the observing eye. As a result of this blockage, i.e., the inability of the light to be reflected, the eye observes a darkness (non-reflection) where the line or wrinkle is located on the skin.

To prevent the appearance of lines and wrinkles, makeup or foundation formulations have been modified to incorporate pigments which manipulate the light, and modify the appearance of the surface to which it is applied. Light manipulation, therefore, has become an important development in makeup products. Many products use optical diffusing powders or pearls to perfect the appearance of the skin. To prevent the appearance of wrinkles on the skin, the main goal of optically diffusing pigments is to prevent light from being trapped inside the crevice of a wrinkle. An optical light diffusing pigment can be for example, titanium dioxide, which physically fills the crevice but reflects light. As a result the line is masked and not highlighted because of the reflective nature of the titanium dioxide. However, this method has been found to be undesirable because it is too opaque and reflective. Therefore, it has been suggested that pigment not only diffuse light but also have a certain amount of transparency to overcome the mask-like appearance of titanium dioxide. Emmert, R., Dr., "Quantification of the Soft-Focus Effect", Cosmetics & Toiletries, vol. 111, no. 7, p. 57 (1996). A number of conclusions were reached with respect to maximizing the efficiency of an optical light diffusing pigment. To begin, it is recommended that light absorption be minimized. The total transmissivity has to be high because transparent materials appear natural. However, the nature of the transmitted light has to be diffuse such that the light transmitted appears to be evenly distributed across the entire area of the observed skin (i.e., refraction). Specular reflection, i.e., light reflected as with a mirror, should be minimized. It is believed that luster increases the appearance of wrinkles.

In general, it has been accepted that glittery and pearly type pigments are not useful in traditional type makeup or foundations. These pigments, which exhibit high specular reflection, are used primarily in special cosmetic products that are considered alternative or "funky". They are used for special occasions, or by a small group of "trendy" users. However, they are not used broadly in makeup products for daily use by the mainstream user. The present invention, however, contrary to the widespread belief that these types of pigments would increase the appearance of wrinkles, and therefore, be undesirable, has surprisingly found that, in combination with a number of different types of optical altering pigments, highly reflective pigments can be an essential part of an integrated pigment system designed to reduce the appearance of fine lines and wrinkles on the skin.

SUMMARY OF THE INVENTION

The present invention is a composition which comprises a first platelet of alumina treated with a metal oxide in combination with at least one second platelet treated with at least one spherical scattering component in a cosmetically or pharmaceutically acceptable vehicle. The compositions of the present invention optically blur the appearance of lines, wrinkles, deformations, and discolorations on the skin surface. As a result of the blurring, observation of these skin flaws is prevented. The combined pigments also provide a natural skin color that closely matches the skin tone of the user. The spherical scattering component can be a spherical silica which also may be covered by a layer of titanium dioxide ($TiO_2$). Because of their shimmering and glittery appearance, these pigments are not known to be formulated in a foundation for daily wear. Surprisingly, it has been found that this combination of platelets, without reliance on the traditional amount of metal oxides used in daily wear foundations, is suitable as a pigment for a foundation that closely matches the natural color of the skin. Therefore, the present invention includes compositions that are substantially free of metal oxides. It has been surprisingly found that topical application of these compositions to the skin causes the appearance of skin flaws to be minimized or prevented from being visible in an everyday makeup formulation.

The present invention also includes methods of preventing the appearance of fine lines and wrinkles on the skin by blurring their ability to be observed. The alumina platelet treated with metal oxide and the platelet treated with the spherical scattering component are blended together based on their ability to manipulate light and provide a natural skin tone color. This combination of pigments when applied to the skin surprisingly produces a diffused reflection of light such that the observer views a smooth and flawless skin surface. The appearance of lines, wrinkles, minor deformations and minor discolorations on the skin are prevented from being visible. The compositions of the present invention optimize the optical diffusion of light and cause the appearance of lines, wrinkles, deformations and other discolorations to substantially vanish. As a result, the natural skin color is seen as smooth and flawless, and the coverage is sufficient to reduce the appearance of redness and other skin discolorations.

DETAILED DESCRIPTION OF THE INVENTION

The combination of pigments in the present invention creates a mosaic of color on a microscopic level (like that of a checkerboard), that when viewed by the natural eye of an observer, appears as a blend of color and scattered light which obscures the ability to see lines, wrinkles, deformations and discolorations on the skin and renders them substantially invisible. The present invention comprises the first platelet of alumina treated with metal oxide, and the second platelet treated with a spherical scattering component. Together, the two different platelets form the mosaic which gently reflects light and matches the natural color of the skin. Each individual platelet is known; however, they each by themselves have drawbacks when used in a daily wear makeup or foundation. Generally, these pigments are not used in traditional makeup formulations intended for daily use because they are not suitable. The alumina-based pigment, for example, is a metallic pigment that achieves complete or near complete reflection. This highly intensive reflection does not look good on the skin as an everyday foundation. It does not match skin tone, and also does not adequately reduce the appearance of skin flaws. Because of the intense reflection, wrinkles are appear more noticeable. Pigments which are capable of specular reflection are shimmery or metallic looking, and therefore, are not typically selected for use in a natural looking makeup or foundation as in the present invention. These types of pigments are suited for makeup products used at times that glitter is desirable. These times are usually holidays and special occasions, like weddings, graduations or other special ceremonies when a sparkle and shine is desirable for the occasion. This is not the purpose of a daily wear foundation.

Although these pigments alone are not suitable for a foundation that matches the natural tone of the skin, in combination with the other platelet component of the present invention, the high glitter of the alumina based pigment is toned down. The combined pigments resemble the natural tone of the skin, and lines, wrinkles and other types of blemishes appear to substantially vanish. The metallic, pearly, and glittery appearance of the alumina platelet is due to its ability to reflect light completely or substantially. The alumina platelet treated with metal oxide produces a deep red and brown finish that is mirror-like (i.e., it is shimmery). Preferably, the alumina platelet is treated with iron oxide and is available commercially from Cardre Inc., South Plainfield, N.J., as Pearl Copper 1000. It is a brown lustrous powder (similar to a rubbed penny) and has a particle size of about 10 to about 20 microns, preferably about 14 to 18 microns. The alumina-based pigment of the present invention is preferred because it produces a metallic effect unlike traditional pearl pigments. The alumina platelet is a planar mirrored particle that is copper colored rather than a tone superimposed with color. When the alumina platelet is combined with other platelet materials or interference pigments in a topical cosmetic or pharmaceutical composition, the appearance of flaws in the skin is altered. The alumina platelets provide color and a metallic look to the mosaic of platelets blended and balanced in the present invention. The alumina platelet is present in an amount of about 0.1 to about 10.0 percent by weight of the composition. Preferably, it is about 0.5 to about 5.0 percent. The other part of the mosaic is the flat finish pigments provided by the second platelet treated with the spherical scattering component.

The second platelet can be, for example, mica, bismuth oxychloride, sericite, alumina, aluminum, copper, bronze, silver or silica. The spherical scattering component can be spherical powders that achieve a soft focus look such as calcium aluminum borosilicate, PMMA, polyethylene, polystyrene, methyl methacrylate crosspolymer, nylon-12, ethylene/acrylic acid copolymer, boron nitride, Teflon, or silica. Examples of available platelets with soft focus materials incorporated include products available from Ikeda (Velvetveil) a mica coated with spherical silica beads, (Soft Vision) a mica coated with silica beads and further coated with $TiO_2$, (Ganzpearls GSC-30SR, and GSC-30MC) a sericite and crosslinked polystyrene, and a mica and crosslinked polystyrene, respectively. The second platelet is present in a total amount of about 0.1 to about 10.0 percent, preferably about 0.2 to about 5.0 percent. When the second platelet is Soft Vision the haze is about 70 to 90 percent (ratio of diffused light to total transmission of light), total transmission of light is about 60 to 80 percent, and the haze is greater than the total transmission of light.

In one embodiment, the composition also comprises a standard interference pigment. Interference pigments, for purposes of the present specification and claims, are defined as thin platelike layered particles having a high refractive index, which, at a certain thickness, produce interference colors, resulting from the interference of typically two, but occasionally more, light reflections, from different layers of the plate. The most common examples of interference pigments are micas layered with about 50 to 300 nm films of $TiO_2$, $Fe_2O_3$, or $Cr_2O_3$. Such pigments are often pearlescent. Pearl pigments reflect, refract and transmit light because of the transparency of pigment particles and the large difference in the refractive index of mica platelets and, for example, the titanium dioxide coating. The reflected light appears as a luster, because light is split by pigment particles at different depths to create a multidimensional shimmer, commonly referred to as pearlescent. The pigments are very reflective, and as mentioned above, are not suitable alone in a makeup product designed to resemble the natural skin tone.

Useful interference pigments are available commercially from a wide variety of suppliers, for example, Rona (Timiron™ and Dichrona™), Presperse (Flonac™), Englehard (Duochrome™), and Kobo (SK-45-R and SK-45-G). Examples of preferable interference pigments are Flonac MS-30C, mica treated with $TiO_2$ and iron oxide (yellow), and MU-10C, mica treated with $TiO_2$ (white). Preferably, interference pigments of different colors or types are combined in the present invention to blend an appropriate shade or intensity of color to match the natural skin tone. The size of the interference pigment can be varied, depending upon the effect desired. Generally, a smaller pigment is less pearly, and therefore preferred, as the larger pigments will confer a substantial amount of sparkle. A useful size range of the interference particles is from about 1 to about 200μ, and preferably is about 3 to about 100μ. The interference pigment is used in an amount of from about 0.05 percent to about 50 percent by weight, with the high end of the range being most appropriate for use in a pressed powder product. However, in most types of products, the amounts of interference pigment will range from about 0.5 percent to about 20 percent, the lower end of the range being used in products using no non-interference pigments or lightly pigmented products, and the higher end of this range being used in more heavily pigmented products. Also, when the vehicle is a water-in-oil or water-in-silicone emulsion, it may be desirable to coat the alumina platelet, the second platelet or the interference pigments with a hydrophobic coating, or other suitable coating to facilitate wetting out. Thus, pearl pigments may be uncoated or coated.

The interference pigments may also be coated to improve the feel of the pigment on the skin. The coating of, for example, spherical powders (on the exterior surface of the pigment) can roll between the surface of the mica and the skin. Even though the mica can be treated to improve its color, feel, stability, and light diffusion properties, the resulting look is unnatural, flat and dull. Because light bounces off the spherical powders in so many different directions, some of the light bounces back into the system of spherical powders and is lost. Therefore, this component alone is also not desirable in a makeup or foundation composition.

In the present invention, the presence of interference pigments assists in the color adjustment of the alumina platelets. Together the pigments and the platelets produce a sum of reflected light off of the skin that appears gentle and soft and blurs the flaws of the skin. Even though more light bounces off the skin and back toward the eye observing the skin surface, the skin looks flawless and luminous from many directions and angles because the second platelet diffuses light bounced off of the skin by the alumina platelet and the interference pigments. Instead of light being trapped in crevices of wrinkles and creating dark lines, the overall net effect of the blended mosaic of pigments and platelets softens the appearance of imperfections and blemishes, and camouflages redness or other discolorations with the color which matches the natural skin tone.

The combination of the alumina platelets, platelets treated with the spherical scattering component and standard interference pigments, when applied to the skin, provides a natural looking appearance. Thus, the compositions of the present invention are substantially free of metal oxides because the color is provided by the alumina platelet in combination with the other components. As used in the present specification and claims, substantially metal oxide free means less than about 7 percent metal oxide, and preferably less than about 5 percent metal oxide. However, because of the many varied skin tones and colors, for a foundation, or other makeup product to match the skin, it may be desirable to add a non-interference pigment to fine tune the closeness of the color to the wearer's skin. Thus, although the present invention achieves color, this fine-tuning is provided by the presence of at least one non-interference pigment. The amount of non-interference pigments used in the present invention is less than the amount used in tradition because unlike traditional foundations which rely almost entirely on metal oxides to provide color, the present invention produces a natural color that matches skin tone with the alumina platelet and the interference pigment. Therefore, unlike the look seen with traditional foundations, which contain high amounts of metal oxides (about 20 percent, for example,) which get trapped in lines and wrinkles, the skin appears flawless with the alumina-based pigment blended with the other components. Further, traditional foundation formulae containing lower amounts of pigment as used in the present invention are sheer and unable to provide the coverage achieved with the present invention. The coverage experienced with the present invention is full without looking ashy or causing a buildup in the lines, wrinkles, and other skin flaws.

Inorganic pigments, organic pigments, or a combination thereof can be used as the non-interference pigment. Examples of useful inorganic pigments include iron oxides (yellow, red, umber, brown or black), ferric ammonium ferrocyanide (blue), manganese violet, ultramarine blue, chrome oxide (green), talc, lecithin modified talc, zeolite, kaolin, lecithin modified kaolin, titanium dioxide (white), zinc oxide and mixtures thereof. Metal oxides, particularly iron and titanium oxides, and kaolin are preferred non-interference pigments in the composition of the invention. In addition to providing color to match the color of the skin, titanium dioxide, zinc oxide, and iron oxide function as particulate inorganic sunscreens.

Organic pigments can include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof. Water soluble colorants (such as FD&C Blue #1), oil soluble colorants (such as D&C Green #6), and stains, such as bromo dyes and fluorescein dyes can also be employed. The amount and type of the non-diffusing pigment used will vary depending upon the nature of the final product and the desired intensity of color; generally, however, the amount of non-diffusing pigment will be about 1 to about 10 percent, and preferably about 1 to about 5 percent, by weight of the total composition. In addition, microfine particulate pigments can be used at somewhat higher levels than those of normal particle size without significantly increasing the level of opacity of the composition on the skin can.

The blended pigment and platelet components of the present invention can be used in any type of skin treatment or makeup product. Skin treatment products, such as lip products, acne treatments, moisturizers, anti-aging products, lifting treatments, cellulite treatments and eye treatments, will ordinarily contain only the metal oxide treated alumina platelet blended with the second platelet treated with the scattering component; however, makeup products will typically contain the additional standard interference and non-interference pigment. The makeup products of the invention include, but are not limited to, foundations, blushes, pressed or loose powders, concealers, bronzers, eyeshadows, eyeliners, lipsticks, and lipglosses. The products of the invention can take any form which is typical of cosmetic products, for example, hot pour formulations, water-in-oil emulsions, oil-in-water emulsions, gels, sticks, sprays, anhydrous formulations, and pressed or loose powders. There is no limitation on the type of vehicle that can be employed. In particular, the preferred identity of the vehicle will be largely controlled by the type of product into which the components are to be incorporated. For a liquid foundation, for example, a water-in-oil emulsion is preferred for aesthetic reasons, and although the oil portion of the vehicle can be any which is typically used for this purpose, it is preferred that the oil component comprise a silicone oil, either volatile or non-volatile. Preferably, the present invention is used in a liquid or powder foundation.

The formulation also can comprise other components that may be chosen depending on the carrier and/or the intended use of the formulation. Additional components include, but are not limited to, water soluble sunscreens (such as Eusolex 232); oil soluble sunscreens (such as octyl methoxycinnamate); and organic sunscreens (such as camphor derivatives, cinnamates, salicylates, benzophenones, triazines, PABA derivatives, diphenylacrylate derivatives, and dibenzoylmethane derivatives.); antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/Eicosene copolymer); water soluble film-formers (such as hydroxypropyl methylcellulose); oil-soluble film formers (such as hydrogenated C-9 Resin); moisturizing agents, such as cholesterol; cationic polymers (such as Polyquatemium 10); anionic polymers (such as xanthan gum); pigment wetting agents, such as Arlacel™ P100, or Emerest™ 2452; vitamins (such as tocopherol); and the like.

The compositions can also encompass one or more active components, and as such can be either cosmetic or pharmaceutical compositions. Examples of useful actives include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, anti-asthmatic agents and bronchodilators, sunscreen agents, antihistamine agents, skin lightening agents, depigmenting agents, wound-healing agents, vitamins, corticosteroids, tanning agents, sunscreens or hormones. More specific examples of useful active agents include retinoids such as retinol, and esters, acids, and aldehydes thereof; ascorbic acid, and esters and metal salts thereof, tocopherol and esters and amide derivatives thereof; shark cartilage; milk proteins; alpha- or beta-hydroxy acids; DHEA and derivatives thereof; topical cardiovascular agents; clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, hydrocortisone, hydrocortisone 21-acetate, hydrocortisone 17-valerate, hydrocortisone 17-butyrate, betamethasone valerate, betamethasone diproprionate, triaminolone acetonide, fluocinonide, clobetasol, proprionate, benzoyl peroxide, crotamiton, propranolol, promethazine, and mixtures thereof.

The invention is further illustrated by the following non-limiting examples:

EXAMPLE I

The following is a liquid foundation composition according to the present invention:

| Ingredient | Amount |
|---|---|
| Phase I | |
| Phenyl Trimethicone | 10.0 |
| TiO2 | 1.8 |
| Red Oxide | 0.1 |
| Yellow Oxide | 0.5 |
| Phase II | |
| Dimethicone copolyol | 5.0 |
| Cyclomethicone | 30.0 |
| Silicone HL 88 | 1.5 |
| Dimethicone | 5.0 |
| Parabens | 0.2 |
| Phase III | |
| Pearl Copper 1000 | 2.0 |
| Flonac MS-30C | 2.5 |
| Flonac MU-10C | 2.0 |
| Soft Vision | 1.0 |
| Phase IV | |
| Distilled Water | 32.0 |
| Butylene glycol | 5.0 |
| Magnesium sulfate | 0.2 |
| Laureth-7 | 0.2 |
| Phenoxyethanol | 1.0 |

EXAMPLE II

The following is a powder foundation composition according to the present invention.

| Ingredient | Amount |
|---|---|
| Phase I | |
| Talc | 70.0 |
| Mica | 5.0 |
| Phase II | |
| Talc | 10.0 |
| Parabens | 0.2 |
| Trisodium EDTA | 0.1 |
| Phase III | |
| Yellow Oxide | 0.5 |
| Octyl Palmitate | 1.0 |
| Cetyl Octanoate | 1.0 |
| Phase IV | |
| Pearl Copper 1000 | 5.0 |
| Flonac MS-30C | 5.2 |
| Soft Vision | 2.0 |

What is claimed is:

1. A composition comprising a pigment having a first platelet of alumina treated with an metal oxide and blended with at least one second platelet treated with at least one spherical scattering component in a cosmetically or pharmaceutically acceptable vehicle.

2. The composition of claim 1 further comprising at least one standard interference pigment.

3. The composition of claim 1 wherein the second platelet is selected from the group consisting of mica, bismuth oxychloride, sericite, alumina, aluminum, copper, bronze, silver or silica.

4. The composition of claim 1 wherein the spherical scattering component is selected from the group consisting of calcium aluminum borosilicate, polymethylmethacrylate borosilicate, polyethylene, polystyrene, methyl methacrylate crosspolymer, nylon-12, ethylene/acrylic acid copolymer, boron nitride, teflon, or silica.

5. The composition of claim 1 wherein the alumina platelet is treated with iron oxide.

6. The composition of claim 1 in which the alumina-based pigment comprises greater than about 90 percent iron oxide and less than about 10 percent alumina.

7. The composition of claim 6 in which the alumina-based pigment has an average particle size of about 10 to about 20 microns.

8. The composition of claim 1 further comprising less than about 7 percent of a non-interference pigment.

9. The composition of claim 8 in which the non-interference pigment is a metal oxide or mixtures thereof.

10. The composition of claim 8 in which the non-interference pigment is less than about 5 percent.

11. The composition of claim 9 wherein the non-interference pigment further comprises at least one organic pigment.

12. The composition of claim 11 in which the organic pigment is selected from the group consisting of phthalocyanine blue and green pigment, diarylide yellow and orange pigments, azo-type red and yellow pigments, lakes, fluorescein dyes, and bromo dyes.

13. The composition of claim 1 which is selected from the group consisting of a powder foundation, a liquid foundation, a skin care product, and a moisturizer.

14. A substantially free metal oxide makeup foundation comprising a first platelet of alumina treated with a metal oxide, at least one second platelet treated with at least one spherical scattering component, at least one standard interference pigment, and a cosmetically or pharmaceutically acceptable vehicle.

15. The composition of claim 14 in which the alumina platelet has an average particle size of about 10 to 20 microns, and the platelet is treated with an iron oxide.

16. The composition of claim 14 further comprising less than about 7 percent non-interference pigment.

17. The composition of claim 16 wherein the non-interference pigment is less than about 5 percent.

18. A substantially free metal oxide composition comprising a) at least one first platelet of alumina treated with a metal oxide, b) a second platelet treated with a spherical silica and a layer of titanium dioxide surrounding the silica, c) at least one standard interference pigment, and d) a cosmetic or pharmaceutical carrier.

19. The composition of claim 18 further comprising less than about 7 percent of a non-interference pigment.

20. A method of blurring the appearance on the skin of fine lines and wrinkles which comprises applying to the skin the composition of claim 1.

21. A method of blurring the appearance on the skin of fine lines and wrinkles which comprises applying to the skin the composition of claim 14.

* * * * *